(12) United States Patent
Dahl

(10) Patent No.: US 11,220,498 B2
(45) Date of Patent: Jan. 11, 2022

(54) NEUROPROTECTIVE AMINOTHIAZOLES

(71) Applicant: Russell Dahl, Saint John, IN (US)

(72) Inventor: Russell Dahl, Saint John, IN (US)

( * ) Notice: Subject to any disclaimer, the term of this patent is extended or adjusted under 35 U.S.C. 154(b) by 0 days.

(21) Appl. No.: 16/699,681

(22) Filed: Dec. 1, 2019

(65) Prior Publication Data

US 2020/0190078 A1    Jun. 18, 2020

Related U.S. Application Data

(60) Provisional application No. 62/774,198, filed on Dec. 1, 2018.

(51) Int. Cl.
*C07D 417/14* (2006.01)
*A61P 25/28* (2006.01)
*C07D 417/04* (2006.01)

(52) U.S. Cl.
CPC ............ *C07D 417/14* (2013.01); *A61P 25/28* (2018.01); *C07D 417/04* (2013.01)

(58) Field of Classification Search
CPC ..... A61P 25/28; C07D 215/40; C07D 401/04; C07D 401/12
See application file for complete search history.

(56) References Cited

U.S. PATENT DOCUMENTS

2008/0039629 A1*  2/2008  Ramesh ............... A61K 31/429
                                                          546/156

OTHER PUBLICATIONS

Yang et al., Protein SUMOylation modification and its associations with disease, 7 Open Biol. 1-18 (2017) (Year: 2017).*
Krajnak & Dahl, 28 Bioorg. & Med. Chem. Letts. 405-409 (2018) (available online Dec. 13, 2017) (Year: 2017).*

* cited by examiner

*Primary Examiner* — Timothy R Rozof

(57) ABSTRACT

Disclosed herein are methods and compositions comprising compounds capable of activating and increasing protein SUMOylation. Disclosed herein are methods and compositions comprising compounds capable of showing neuroprotective and cytoprotective effects when administered to injured cells. Also disclosed are methods comprising these compounds for treating neuronal or neurological disorders, including Alzheimer's disease, Parkinson's disease, Huntington's disease, fronto-temporal dementia, chronic traumatic encepholopathy, traumatic brain injury, or stroke.

4 Claims, No Drawings

NEUROPROTECTIVE AMINOTHIAZOLES

This application claims the benefit of priority from U.S. Provisional Application No. 62/774,198, filed Dec. 1, 2018, which is incorporated by reference herein in its entirety.

BACKGROUND

There are no approved drugs that provide a neuroprotective effect for the treatment of neurodegenerative diseases and brain injury including Alzheimer's disease (AD), Parkinson's disease (PD), Huntington's disease, fronto-temporal dementia, traumatic brain injury (TBI), stroke, and CTE (chronic traumatic encephalopathy). Thus, there is need for the development of neuroprotective compounds that can be administered to treat these conditions.

Neuron death plays a central role in many diseases that currently have no pharmacological therapeutics available (Repici, M.; Mariani, J.; Borsello, T. Methods Mol. 2007, 399, 1-14). Thus, neuroprotection has been a major goal of neuroscience the pharmaceutical industry, specifically relevant to diseases involving brain injury resulting in neuron loss or neurodegenerative disease. Neuroprotection has the potential to provide effective treatments for stroke, CNS trauma, Alzheimer's disease (AD), and Parkinson's disease (PD), but there are no approved therapies that demonstrate neuroprotection. There is significant economic and social burdens related to these diseases. CNS trauma and related maladies have estimated costs of $106 billion annually in the US alone (Samantaray, S.; Thakore, N. P.; Matzelle, D. D.; Varma, A.; NarBanik, N. L. The Open Drug Discovery Journal. 2010, 2, 174-180). AD affects over 5 million Americans with annual economic burdens in the US of over $180 billion annually. PD-related costs are over $6 billion a year (de Lau, L. M.; Breteler, M. M. Lancet Neurol. 2006, 5, 525-535). Clearly, there is an urgent need for therapies with neuroprotective effects.

Increased protein conjugation with small ubiquitin-like modifier (SUMO) proteins has been established by numerous studies as an endogenous neuroprotective mechanism in neurons (Datwyler, A. L.; Lättig-Tünnemann, G.; Yang, W.; Paschen, W.; Lee, S. L.; Dirnagl, U.; Endres, M.; Harms, C. J. Cereb. Blood Flow Metab. 2011, 31, 2152-2159). Small molecule SUMOylation enhancers would thus provide drugs to treat these important disorders.

SUMO is a small protein that covalently attaches to proteins via an enzymatic cascade that is analogous to the ubiquitin pathway. This includes an E1 enzyme (SUMO activating enzyme, SAE), an E2 enzyme (Ubc9), and, sometimes, various E3 ligases (Melchior, F.; Schergaut, M.; Pichler, A. Trends Biochem. Sci. 2003, 28, 612-618). One function of this conjugation is to modulate protein-protein interactions. However, global increases in SUMOylation levels mark the response to neuronal insult caused by CNS trauma and neurodegenerative pathogenesis and provide neuroprotection (Tempé, D.; Piechaczyk, M.; Bossis, G. Biochem. Soc. Trans. 2008, 36, 874-878). SUMO conjugation has been established as an endogenous neuroprotective strategy in multiple models (Lee, Y. J.; Castri, P.; Bembry, J.; Maric, D.; Auh, S.; Hallenbeck, J. M. J. Neurochem. 2009, 109, 257-267). Also, SUMOylation is activated in hibernation as a neuroprotective response to decreased bloodflow and nutrient deprivation (Lee, Y. J.; Miyake, S.; Wakita, H.; McMullen, D. C.; Azuma, Y.; Auh, S.; Hallenbeck, J. M. J. Cereb. Blood Flow Metab. 2007, 27, 950-962). Massive increases in SUMO and SUMOylation machinery are seen in animal models of ischemia (Yang, W.; Sheng, H.; Homi, H. M.; Warner, D. S.; Paschen, W. J. Neurochem. 2008, 106, 989-999). Overexpression of SUMO components and increased SUMOylation leads to a reduction in cell loss from stressors such as oxygen and glucose deprivation (OGD) and ischemic conditions, while knock down of SUMO in a cellular model made cells more susceptible to OGD-induced cell death (Lee, Y. J.; Castri, P.; Bembry, J.; Maric, D.; Auh, S.; Hallenbeck, J. M. J. Neurochem. 2009, 109, 257-267). Increased SUMO conjugation has also been seen concurrently with increased ubiquitination in neuronal injury as focal cerebral ischemia increased both protein ubiquitination and SUMOylation in various protein aggregates in the CNS (Hochrainer, K.; Jackman, K.; Benakis, C.; Anrather, J.; Iadecola, C. J. Cereb. Blood Flow Metab. 2015, 35, 1-5). Also, SUMOylation has been shown to play a protective effect in the brains of transgenic mice following ischemic damage (Lee, Y. J.; Mou, Y.; Maric, D.; Klimanis, D.; Auh, S.; Hallenbeck, J. M. PLoS One. 2011, 6, e25852).

While inhibition of the various SUMO pathway components to reduce protein SUMOylation has been targeted as a strategy for various diseases including cancer, viral infection, and cystic fibrosis (Licciardello, M. P.; Kubicek, S. Pharmacol. Res. 2016, 107, 390-397; Ahner, A.; Frizzell, R. A. Curr. Drug Targets. 2015, 16, 965-975), relatively few reports of pharmacological activation of SUMO conjugation are currently available. These include activators of SUMO conjugation discovered via the inhibition of microRNAs 182 and 183 (Bernstock, J. D.; Lee, Y. J.; Peruzzotti-Jametti, L.; Southall, N.; Johnson, K. R.; Maric, D.; Volpe, G.; Kouznetsova, J.; Zheng, W.; Pluchino, S.; Hallenbeck, J. M. J. Cereb. Blood Flow Metab. 2016, 36, 426-441). Reported activators were shown to be neuroprotective in an in vitro model of ischemia. Another recent report describes a SUMOylation activator for the substrate protein Sarco/Endoplasmic Reticulum $Ca^{2+}$-ATPase (SERCA) (Kang, S.; Dahl, R.; Hsieh, W.; Shin, A.; Zsebo, K. M.; Buettner, C,; Hajjar, R. J.; Lebeche, D. J. Biol. Chem. 2016, 291, 5185-5198). This increase in SUMO conjugation led to the subsequent activation of SERCA and improved muscle contraction for applications in heart failure. Finally, is the report that includes the subject matter of this application (Krajnak, K.; Dahl, R. Bioorg. Med. Chem. Lett. 2018, 28, 405-409).

Thus, there is a need in the art for novel compounds that can activate SUMOylation and show neuroprotective effects.

DESCRIPTION OF THE INVENTION

The present disclosure provides compositions and methods comprising novel compounds that increase protein SUMOylation. Treatment of injured neurons with the SUMOylation enhancers shows neuroprotective effects toward treating neurodegenerative diseases, such as AD, PD, stroke, ischemia, TBI, and CTE.

Thus, one aspect the disclosure provides compounds of formula I:

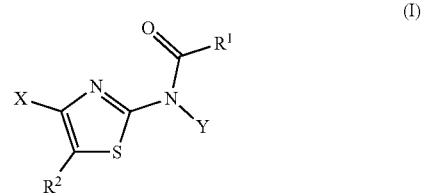

or a pharmaceutically acceptable salt thereof, wherein

Y is hydrogen, $C_{1-6}$ alkyl, or $C_{1-6}$ alkylcarbonyl;

X and $R^1$ are independently $C_{1-6}$ alkyl, cycloalkyl, benzyl, aryl, naphthyl, 2-pyridiyl, 3-pyridiyl, 4-pyridiyl, or heteroaryl, wherein alkyl, benzyl, aryl, or heteroaryl is optionally substituted with 1, 2, 3, 4, or 5 independently selected $R^3$ groups;

$R^2$ is selected from hydrogen, halo, CN, nitro, hydroxy, $C_{1-6}$ alkyl, $C_{1-6}$ haloalkyl, $C_{1-6}$ alkoxy, $C_{1-6}$ haloalkoxy, amino, $C_{1-6}$ alkylamino, di-$C_{1-4}$-alkylamino, carboxy, carbamoyl, $C_{2-6}$ alkylcarbamoyl, di($C_{1-4}$ alkyl)carbamoyl, $C_{1-6}$ alkylcarbonyl, $C_{1-6}$ alkoxycarbonyl, $C_{1-6}$ alkylcarbonyloxy, $C_{1-6}$ alkylsulfonyl, $C_{1-6}$ alkylcarbonylamino, $C_{1-6}$ alkylsulfonylamino, aminosulfonyl, $C_{1-6}$ alkylaminosulfonyl, di-$C_{1-4}$ alkylaminosulfonyl, aminosulfonylamino, $C_{1-6}$ alkylaminosulfonylamino, and di-$C_{1-4}$ alkylaminosulfonylamino; wherein each is optionally substituted at a suitable position with 1, 2, or 3 groups independently selected from halo, CN, hydroxy, $C_{1-3}$ alkyl, $C_{1-3}$ alkoxy, amino, $C_{1-3}$ alkylamino, and di-$C_{1-3}$-alkylamino;

$R^3$ is selected from halo, CN, nitro, hydroxy, $C_{1-6}$ alkyl, $C_{1-6}$ haloalkyl, $C_{1-6}$ alkoxy, $C_{1-6}$ haloalkoxy, amino, $C_{1-6}$ alkylamino, di-$C_{1-4}$-alkylamino, carboxy, carbamoyl, $C_{1-6}$ alkylcarbamoyl, di($C_{1-4}$ alkyl)carbamoyl, $C_{1-6}$ alkylcarbonyl, $C_{1-6}$ alkoxycarbonyl, $C_{1-6}$ alkylcarbonyloxy, $C_{1-6}$ alkylsulfonyl, $C_{1-6}$ alkylcarbonylamino, $C_{1-6}$ alkylsulfonylamino, sulfonylpyrrole, sulfonylpiperidine, sulfonylmorpholine, aminosulfonyl, $C_{1-6}$ alkylaminosulfonyl, di-$C_{1-4}$ alkylaminosulfonyl, aminosulfonylamino, $C_{1-6}$ alkylaminosulfonylamino, di-$C_{1-4}$ alkylaminosulfonylamino, and oxo, wherein each is optionally substituted at a suitable position with 1, 2, or 3 groups independently selected from halo, CN, hydroxy, $C_{1-3}$ alkyl, $C_{1-3}$ alkoxy, amino, $C_{1-3}$ alkylamino, and di-$C_{1-3}$-alkylamino.

In some embodiments, the disclosure provides compounds of formula I, wherein the compounds are selected from the group consisting of:

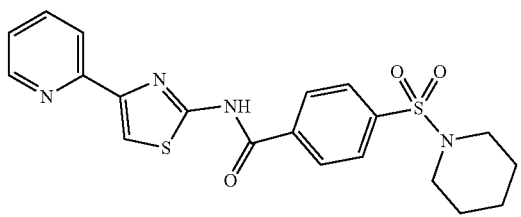

C1

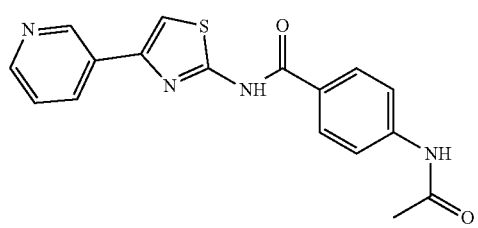

C2

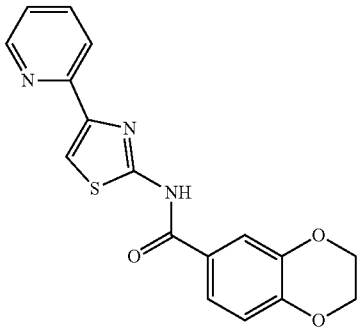

C3

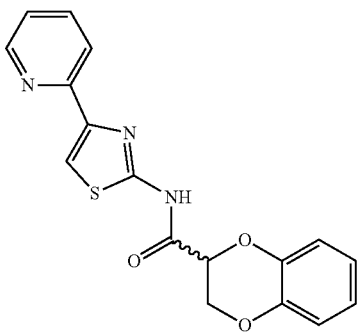

C4

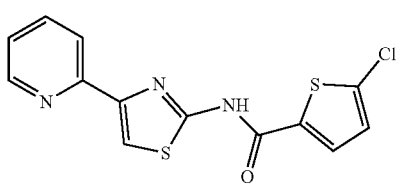

C5

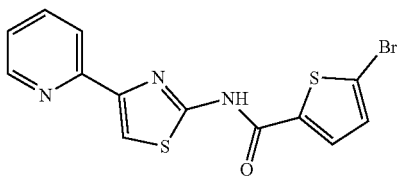

C6 or a pharmaceutically acceptable salt thereof.

The disclosure also provides synthetic intermediates that are useful in making the compounds of formula I. The disclosure also provides methods of preparing compounds of the disclosure and the intermediates used in those methods.

Another aspect of the disclosure provides for pharmaceutical composition comprising a pharmaceutically acceptable carrier, solvent, adjuvant or diluent and one or more compounds of formula I.

In another aspect, the disclosure provides methods for increasing SUMOylation activity in a subject comprising administering to the subject an effective amount of one or more compounds of formula I. In some embodiments, the subject is a human subject.

In another aspect, the disclosure provides methods for treating a neurological or neurodegenerative disorder in a subject comprising administering to the subject an effective amount of one or more compounds of formula I.

In another aspect, the disclosure provides compositions for treating a neurological or neurodegenerative disorder comprising one or more compounds of formula I.

In another aspect, the disclosure provides uses of one or more compounds of formula I for preparing compositions for treating a neurological or neurodegenerative disorder.

In some embodiments, the neurological or neurodegenerative disorder is Alzheimer's disease, Parkinson's disease, Huntington's disease, fronto-temporal dementia, chronic traumatic encepholopathy, traumatic brain injury, or stroke. In some embodiments, the subject is a human subject.

EXAMPLES

The Examples that follow are illustrative of specific embodiments of the invention, and various uses thereof. They are set forth for explanatory purposes only and are not to be taken as limiting the invention.

The preparation of the compounds of the disclosure is illustrated further by the following examples, which are not to be construed as limiting the disclosure in scope or spirit to the specific procedures and compounds described in them. In all cases, unless otherwise specified, the column chromatography is performed using a silica gel solid phase.

Those having skill in the art will recognize that the starting materials and reaction conditions may be varied, the sequence of the reactions altered, and additional steps employed to produce compounds encompassed by the present disclosure, as demonstrated by the following examples.

Starting materials can be obtained from commercial sources or prepared by well-established literature methods known to those of ordinary skill in the art. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the disclosure.

Example 1

Assessing SUMOylation Increase By Compounds

Assay measuring increase in SUMOylation of His-RanGap. We utilized an HTRF assay containing SUMO-E1 (SAE), SUMO-E2 (UBC9), GST-SUMO and His-RanGap, a known SUMO substrate, as well as the respective fluorescent antibodies. The assay was run in 1536-well plate format and the selected activators were chosen based on their ability to increase the FRET signal over a baseline level. In 1536-well white plates, 2 µl of phosphate buffered saline (assay buffer) was dispensed into columns 1 and 2, and 2 µl of Mixture 1 (37.5 nM E1 and 100 nM His-RanGap-1) in assay buffer (50 mM Tris-HCl pH 7.4, 0.3 mM DTT, 10 mM MgCl$_2$, 0.005% Tween-20), was dispensed into columns 3-48. Using a pintool, 70 nl of 2 mM compounds in DMSO was dispensed to columns 5-48 and 70 nl of DMSO was dispensed to columns 1-4. Using the Thermo Scientific MultiDrop Combi, 2 µL of Mixture 2 (20 mM ATP, 12.5 nM E2 and 30 nM GST-SUMO in buffer) was dispensed to all wells and incubated for 30 min. at room temperature followed by 1 µl of 500 mM KF. Plates were read on a PheraStar in a HTRF mode (Ex: 337 nm; Em: 620/665 nm). The ratio of fluorescence 665 over 620 was utilized as a readout of the assay. Increase in SUMOylation was calculated by comparison to baseline level. Measurements were done in triplicate.

TABLE 1

Increase in % SUMOylation of known SUMO substrate His-RanGap with compounds.

| COMPOUND | % INCREASE IN SUMOylation over endogenous baseline level |
|---|---|
| C1 | D |
| C2 | A |
| C3 | A |
| C4 | D |
| C5 | B |
| C6 | C |

A = 10%-20% increase, B = 21%-30% increase; C = 31%-40% increase; and D = 40%-60% increase in SUMOylation over baseline levels.

Example 2

Assessing Neuroprotective and Cytoprotective Properties of SUMOylation Increasing Compounds Ability of compounds to rescue CSM14.1 neurons from thapsigargin-induced cell death. To assess the ability of the compounds to rescue neurons from ER stress-induced cell death, the rat striatel neuroprogenitor cell line CSM14.1 was used. Endoplasmic reticulum (ER) stress has been established as the major cause of neuronal loss in stroke, ischemia, and neurodegeneration (Tajiri, S.; Oyadomari, S.; Yano, S.; Morioka, M.; Gotoh, T.; Hamada, J. I.; Ushio, Y.; Mori, M. *Cell Death Differ.* 2004, 11, 403-415; Kohno, K.; Higuchi, T.; Ohta, S.; Kumon, Y.; Sakaki, S. *Neurosci. Lett.* 1997, 224, 17-20; Iadecola, C.; Zhang, F.; Casey, R.; Nagayama, M.; Ross, M. E. *J. Neurosci.* 1997, 17, 9157-9164). Thus, we used the known ER stress-causing agent thapsigargin (TG) to model the compromised state in vitro. TG causes 100% cell death in most cases, and compounds were assessed for neuroprotection by measuring cell viability when dosed at 10 µM. CSM14.1 cells were recovered from cultures by trypsinization and plated in 96-well plates and incubated overnight at 32° C. 5 µl of test compound was added to achieve a final concentration of 15 µg/ml. Salubrinal and DMSO without compound were used as positive and negative controls, respectively. After 2 h of preincubation, TG-containing DMEM was added to give a final concentration of 15 µM and incubated for an additional 20 h. Cell viability was assessed by a cellular ATP content assay (ATPlite, PerkinElmer Life Sciences).

TABLE 2

Viability of CSM14.1 neuronal cells after injury with ER-stress causing agent thapsigargin (causes ~100% cell death).

| Compound | % CSM14.1 Cell Viability after treatment with 15 µM TG in Presence of 10 µM compound |
|---|---|
| C1 | A |
| C4 | C |
| C6 | C |

A = 40%-50% viability; B = 51%-60% viability; and C = 61%-70% viability of CSM14.1 neurons.

Ability of compounds to rescue BGMK cells from thapsigargin-induced cell death. To assess an orthogonal cell line and further validate the ability of SUMOylation activators to rescue varied cell types, the compounds were also profiled for cytoprotection in BGMK cells. Again, we used the known ER stress-causing agent thapsigargin (TG) to model the compromised state in vitro. BGMKs were subcultured at 1.2×104 cells/ml. Wells treated with compound were done so for 2 hr. TG was at a concentration of 0.15 µM then added and incubated for 24 hrs. After treatment, all cells were washed and fed fresh DMEM complete media and CCK-8 development vehicle, incubated for 2 hr, and absorbance was measured to assess viability. Controls were DMSO (0% viability) and Salubrinal (47% viability).

TABLE 3

Viability of BGMK cells after injury with ER-stress causing agent thapsigargin (causes ~100% cell death).

| Compound | % BGMK Cell Viability after treatment with 15 µM TG in Presence of 10 µM compound |
|---|---|
| C3 | C |
| C4 | D |
| C5 | B |
| C6 | D |

A = 30%-40% viability; B = 41%-50% viability; C = 51%-60% viability, and D = 61%-85% viability of BGMK cells.

Synthetic methods for the compounds C1-C6 are as follows:

N-(4-(Pyridin-2-yl)thiazol-2-yl)-2,3-dihydrobenzo[b][1,4]dioxine-2-carboxamide (C4). 4-(Pyridin-2-yl)thiazol-2-amine (177 mg, 1.0 mmol) was dissolved in N,N-dimethylformamaide (DMF, 10 mL) and to this mixture was added triethylamine (TEA) with stirring (0.167 mL, 1.2 mmol). 2,3-Dihydrobenzo[b][1,4]dioxine-2-carbonyl chloride (199 mg, 1.0 mmol) was added dropwise and stirring was continued overnight. Water was added (100 mL) and this mixture was extracted with 2 volumes of ethyl acetate. The organic layers were collected and solvent removed en vacuo. The crude material was purified via silica gel chromatography (EtOAc/Hexane, 30-95%), the product fractions were collected, concentrated and lyophilized to furnish the title compound. ESI-MS m/z calculated for $C_{17}H_{13}N_3O_3S$ [M+H]$^+$: 340. Found 340.

5-Bromo-N-(4-(pyridin-2-yl)thiazol-2-yl)thiophene-2-carboxamide (C6). 4-(Pyridin-2-yl)thiazol-2-amine (177 mg, 1.0 mmol) was dissolved in N,N-dimethylformamaide (DMF, 10 mL) and to this mixture was added triethylamine (TEA) with stirring (0.167 mL, 1.2 mmol). 5-Bromothiophene-2-carbonyl chloride (225 mg, 1.0 mmol) was added dropwise and stirring was continued overnight. Water was added (100 mL) and this mixture was extracted with 2 volumes of ethyl acetate. The organic layers were collected and solvent removed en vacuo. The crude material was purified via silica gel chromatography (EtOAc/Hexane, 30-95%), the product fractions were collected, concentrated and lyophilized to furnish the title compound. ESI-MS m/z calculated for $C_{13}H_8BrN_3OS_2$ [M+H]$^+$: 367. Found 367.

5-Chloro-N-(4-(pyridin-2-yl)thiazol-2-yl)thiophene-2-carboxamide (C5). 4-(Pyridin-2-yl)thiazol-2-amine (177 mg, 1.0 mmol) was dissolved in N,N-dimethylformamaide (DMF, 10 mL) and to this mixture was added triethylamine (TEA) with stirring (0.167 mL, 1.2 mmol). 5-Chlorothiophene-2-carbonyl chloride (181 mg, 1.0 mmol) was added dropwise and stirring was continued overnight. Water was added (100 mL) and this mixture was extracted with 2 volumes of ethyl acetate. The organic layers were collected and solvent removed en vacuo. The crude material was purified via silica gel chromatography (EtOAc/Hexane, 30-95%), the product fractions were collected, concentrated and lyophilized to furnish the title compound. ESI-MS m/z calculated for $C_{13}H_8ClN_3OS_2$ [M+H]$^+$: 322. Found 322.

N-(4-(Pyridin-2-yl)thiazol-2-yl)-2,3-dihydrobenzo[b][1,4]dioxine-6-carboxamide (C3). 4-(Pyridin-2-yl)thiazol-2-amine (177 mg, 1.0 mmol) was dissolved in N,N-dimethylformamaide (DMF, 10 mL) and to this mixture was added triethylamine (TEA) with stirring (0.167 mL, 1.2 mmol). 2,3-Dihydrobenzo[b][1,4]dioxine-6-carbonyl chloride (199 mg, 1.0 mmol) was added dropwise and stirring was continued overnight. Water was added (100 mL) and this mixture was extracted with 2 volumes of ethyl acetate. The organic layers were collected and solvent removed en vacuo. The crude material was purified via silica gel chromatography (EtOAc/Hexane, 30-95%), the product fractions were collected, concentrated and lyophilized to furnish the title compound. ESI-MS m/z calculated for $C_{17}H_{13}N_3O_3S$ [M+H]$^+$: 340. Found 340.

4-(1-Piperidinylsulfonyl)-N-[4-(2-pyridinyl)-2-thiazolyl]-benzamide (C1). 4-(Pyridin-2-yl)thiazol-2-amine (1.0 mmol) was dissolved in N,N-dimethylformamide (DMF, 10 mL) and to this mixture was added triethylamine (TEA) with stirring (0.167 mL, 1.2 mmol). 4-(1-Piperidinylsulfonyl)-benzoyl chloride (1.0 mmol) was added dropwise and stirring was continued overnight. Water was added (100 mL) and this mixture was extracted with 2 volumes of ethyl acetate. The organic layers were collected and solvent removed en vacuo. The crude material was purified via silica gel chromatography (EtOAc/Hexane, 30-95%), the product fractions were collected, concentrated and lyophilized to furnish the title compound. ESI-MS m/z calculated for $C_{20}H_{20}N_4O_3S_2$ [M+H]$^+$: 429. Found 429.

4-(Acetylamino)-N-[4-(3-pyridinyl)-2-thiazolyl]-benzamide (C2). 4-(Pyridin-2-yl)thiazol-2-amine (1.0 mmol) was dissolved in N,N-dimethylformamide (DMF, 10 mL) and to this mixture was added triethylamine (TEA) with stirring (0.167 mL, 1.2 mmol). 4-(Acetylamino)-benzoyl chloride (1.0 mmol) was added dropwise and stirring was continued overnight. Water was added (100 mL) and this mixture was extracted with 2 volumes of ethyl acetate. The organic layers were collected and solvent removed en vacuo. The crude material was purified via silica gel chromatography (EtOAc/Hexane, 30-95%), the product fractions were collected, concentrated and lyophilized to furnish the title compound. ESI-MS m/z calculated for $C_{17}H_{14}N_{14}O_2S$ [M+H]$^+$: 339. Found 339.

Having described the invention in detail and by reference to specific embodiments thereof, it will be apparent that modifications and variations are possible without departing from the scope of the invention defined in the appended claims. More specifically, although some aspects of the present invention are identified herein as particularly advantageous, it is contemplated that the present invention is not necessarily limited to these particular aspects of the invention.

I claim:

1. A method for increasing protein SUMOylation in a subject comprising administering to the subject an effective amount of a compound selected from:

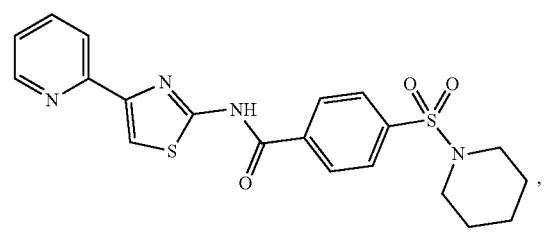

-continued

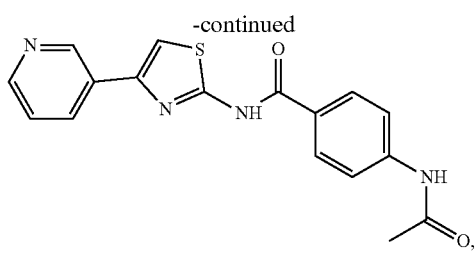

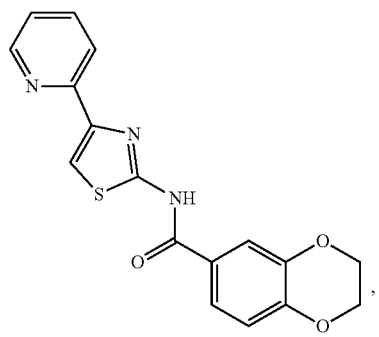

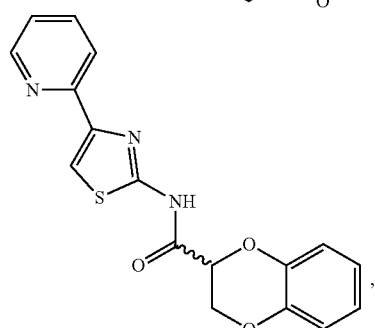

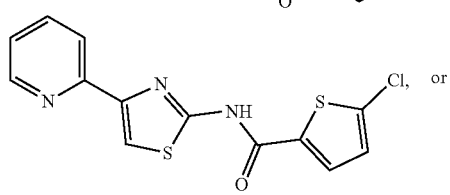

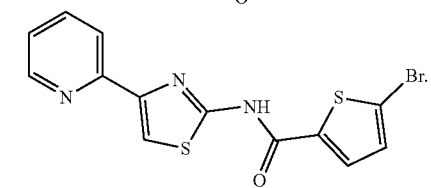

-continued

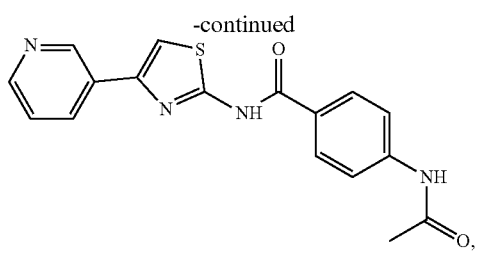

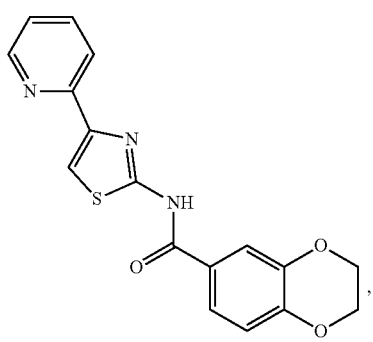

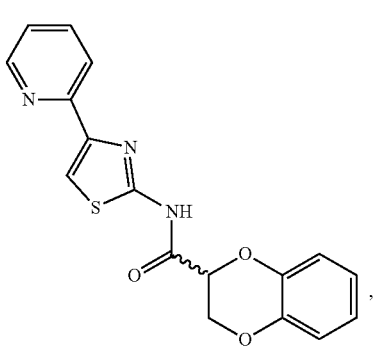

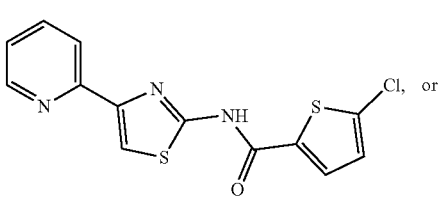

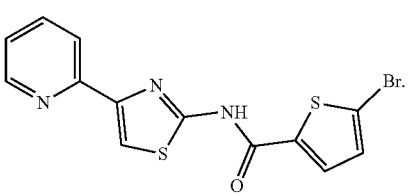

2. The method of claim 1, wherein the subject is a human subject.

3. A method for treating a neurological or neurodegenerative disorder in a subject comprising administering to the subject an effective amount of a compound selected from:

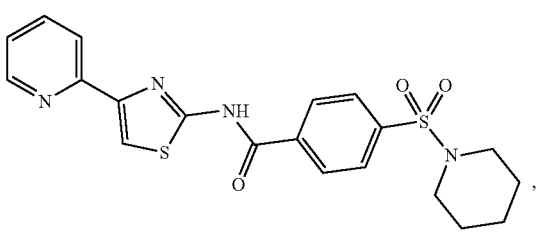

4. The method of claim 3, wherein the neurological or neurodegenerative disorder is Alzheimer's disease, Parkinson's disease, Huntington's disease, fronto-temporal dementia, chronic traumatic encepholopathy, traumatic brain injury, or stroke.

* * * * *